(12) United States Patent
Grasmeder et al.

(10) Patent No.: US 6,537,478 B1
(45) Date of Patent: Mar. 25, 2003

(54) INJECTION MOULDING ARTICLES MADE OF METALLOCENE POLYPROPYLENE

(75) Inventors: John Russell Grasmeder, Dirmstein (DE); Klaus Overthun, Fussgönheim (DE)

(73) Assignee: Basell Polyolefine GmbH, Wesseling (DE)

( * ) Notice: Subject to any disclaimer, the term of this patent is extended or adjusted under 35 U.S.C. 154(b) by 0 days.

(21) Appl. No.: 09/486,634

(22) PCT Filed: Aug. 21, 1998

(86) PCT No.: PCT/EP98/05334

§ 371 (c)(1),
(2), (4) Date: Feb. 29, 2000

(87) PCT Pub. No.: WO99/11678

PCT Pub. Date: Mar. 11, 1999

(30) Foreign Application Priority Data

Sep. 1, 1997 (DE) .......................................... 197 38 051

(51) Int. Cl.$^7$ .......................... B29C 47/00; B65D 85/57
(52) U.S. Cl. .................. 264/328.1; 264/239; 264/297.2; 526/351; 526/348; 428/35.7; 206/308.1
(58) Field of Search ........................ 526/351; 428/35.7; 206/308.1; 264/239, 297.2, 328.1

(56) References Cited

U.S. PATENT DOCUMENTS

| | | | |
|---|---|---|---|
| 5,328,969 A | | 7/1994 | Winter et al. |
| 5,374,752 A | | 12/1994 | Winter et al. |
| 5,377,825 A | * | 1/1995 | Sykes et al. ................. 206/232 |
| 5,455,365 A | | 10/1995 | Winter et al. |
| 5,590,768 A | * | 1/1997 | Hilton et al. ............. 206/308.1 |
| 5,741,563 A | * | 4/1998 | Mehta et al. .............. 428/35.1 |
| 5,775,491 A | * | 7/1998 | Taniyama ................ 206/308.1 |
| 5,782,348 A | * | 7/1998 | Burdett ..................... 206/308.1 |
| 5,998,039 A | * | 12/1999 | Tanizaki et al. ............ 428/516 |
| 6,096,843 A | * | 8/2000 | Saito et al. ................. 526/127 |

FOREIGN PATENT DOCUMENTS

| | | | |
|---|---|---|---|
| CA | 2099214 | | 12/1993 |
| EP | 582 194 | | 2/1994 |
| WO | 97/19980 | | 5/1997 |
| WO | WO97/19991 | * | 6/1997 |

\* cited by examiner

*Primary Examiner*—David W. Wu
*Assistant Examiner*—R. Rabago
(74) *Attorney, Agent, or Firm*—Keil & Weinkauf

(57) ABSTRACT

Homopolymers of propylene or copolymers of propylene with $C_2$14 $C_{10}$-alk-1-enes, which polymers are obtainable by polymerization of the corresponding monomers using metallocene catalysts are used for producing moldings such as injection-molded articles.

6 Claims, No Drawings

INJECTION MOULDING ARTICLES MADE OF METALLOCENE POLYPROPYLENE

The present invention relates to the use of homopolymers of propylene or copolymers of propylene with $C_2$–$C_{10}$-alk-1-enes, which polymers are obtainable by polymerization of the corresponding monomers using metallocene catalysts, for producing moldings, preferably hollow bodies, in particular injection-molded articles.

Plastics, in particular olefin polymers, are processed into moldings using the injection molding technique.

However, such moldings, or the polymers on which they are based, have disadvantages.

Moldings having high transparency, for example made of random copolymers of propylene with other olefins, usually have unsatisfactory stiffness, expressed by the E modulus in accordance with ASTM D882.

On the other hand, moldings having a high stiffness, for example made of homopolymers of propylene, generally have insufficient transparency, measured in accordance with ASTM D1003.

Many of the currently available polyolefins which are employed in injection molding also have unsatisfactory organoleptic properties (unpleasant odor and/or taste of the finished article).

It is an object of the present invention to develop polymers which combine high transparency with, at the same time, good stiffness and which additionally have a low odor and/or taste (good organoleptic properties) and a low proportion of xylene-soluble material, preferably less than 1.5% by weight.

We have found that this object is achieved by the use of homopolymers of propylene or copolymers of propylene with $C_2$–$C_{10}$-alk-1-enes, which polymers are obtainable by polymerization of the corresponding monomers using metallocene catalysts, for producing moldings and injection-molded articles as defined in the claims.

The propylene polymers according to the present invention are propylene homopolymers or copolymers of propylene and an alk-1-ene or a plurality of alk-1-enes selected from the group consisting of ethylene, 1-butene, 1-pentene, 1-hexene, 1-heptene, 1-octene, 1-nonene, 1-decene and 4-methyl-1-pentene, or mixtures of these polymers, where the mixing ratios are not critical. For the purposes of the present invention, copolymers are generally random copolymers.

The propylene homopolymers are essentially isotactic.

The homopolymers of propylene or copolymers of propylene with $C_2$–$C_{10}$-alk-1-enes, having the above-described composition and structure, are obtained by polymerization of the corresponding monomers using metallocene catalysts. Hereinafter, such propylene polymers are referred to as "propylene homopolymers and copolymers according to the present invention".

For the purposes of the present invention, metallocene catalysts are materials which are generally formed by combining a transition metal compound or a plurality of transition metal compounds, preferably of titanium, zirconium or hafnium, which contain at least one ligand which is, in the widest sense, a derivative of the cyclopentadienyl ligand, with an activator, also referred to as cocatalyst or compound capable of forming metallocenium ions, and generally display polymerization activity toward the monomers described. Such catalysts are described, for example, in EP-A 0 545 303, EP-A 0 576 970 and EP-A 0 582 194.

Well suited catalysts are described, for example, in WO 97/19980, page 3, line 16 to page 11, line 17.

Very particularly preferred metallocene components of the catalyst systems are rac-dimethylsilylenebis(2-methylbenzindenyl)zirconium dichloride
rac-dimethylsilylenebis(2-ethylbenzindenyl)zirconium dichloride
rac-dimethylsilylenebis(2-methylindenyl)zirconium dichloride
rac-dimethylsilylenebis(2,4-dimethylindenyl)zirconium dichloride
rac-dimethylsilylenebis(2,4,7-trimethylindenyl)zirconium dichloride
rac-dimethylsilylenebis(2-methyl-4-isopropylindenyl)zirconium dichloride
rac-dimethylsilylenebis(2-methyl-4,6-diisopropylindenyl)zirconium dichloride
rac-dimethylsilylenebis(2-methyl-4-phenylindenyl)zirconium dichloride
rac-dimethylsilylenebis(2-ethyl-4-phenylindenyl)zirconium dichloride
rac-dimethylsilylenebis(2-methyl-4-naphthylindenyl)zirconium dichloride
rac-ethylenebis(2-methylbenzindenyl)zirconium dichloride
rac-ethylenebis(2-ethylbenzindenyl)zirconium dichloride
rac-ethylenebis(2-methylindenyl)zirconium dichloride
rac-ethylenebis(2,4-dimethylindenyl)zirconium dichloride
rac-ethylenebis(2,4,7-trimethylindenyl)zirconium dichloride
rac-ethylene(2-methyl-4-isopropylindenyl)zirconium dichloride
rac-ethylenebis(2-methyl-4,6-diisopropylindenyl)zirconium dichloride
rac-ethylenebis(2-methyl-4-phenylindenyl)zirconium dichloride
rac-ethylenebis(2-ethyl-4-phenylindenyl)zirconium dichloride
rac-ethylenebis(2-methyl-4-naphthylindenyl)zirconium dichloride The preparation of the polypropylene polymers can be carried out in the customary reactors used for the polymerization of olefins, either batchwise or preferably continuously. Suitable reactors are, inter alia, continuously operated stirred vessels or loop reactors; it is also possible, if desired, to use a plurality of stirred vessels or loop reactors connected in series. The polymerization reactions can be carried out in the gas phase, in suspension, in liquid and in supercritical monomers or in inert solvents.

The polymerization conditions are in themselves not critical. Pressures of from 100 to 350,000 kPa, preferably from 100 to 250,000 and in particular from 100 to 100,000 kPa, and temperatures of from 0 to 400° C., preferably from 20 to 250° C. and in particular from 50 to 100° C., have been found to be useful.

The mean molecular weight of the polymers can be controlled by means of the methods customary in polymerization technology, for example by introduction of molecular weight regulators such as hydrogen which leads to a reduction in the molecular weight of the polymer or by variation of the polymerization temperature, where high polymerization temperatures usually likewise lead to reduced molecular weights.

The propylene homopolymers and copolymers according to the present invention generally have a melt flow rate (MFR) measured at 230° C. and a load of 2.16 kg in accordance with DIN 53735 in the range from 10 to 100 g/10 min, preferably in the range from 40 to 80 g/10 min and in particular in the range from 50 to 65 g/10 min.

The molecular weight distribution of the propylene homopolymers and copolymers according to the present invention Mw/Mn, determined by means of GPC at 140° C. in 1,2,4-trichlorobenzene relative to a polypropylene standard, is generally in the range from 1.2 to 3.0, preferably from 1.2 to 2.5.

The molecular weight Mw, the molecular weight distribution Mw/Mn and, in particular, the MFR can also be adjusted by peroxidically initiated degradation of a starting polymer, advantageously in an extruder. This method is known to those skilled in the art.

The propylene homopolymers according to the present invention generally have a melting point, determined by differential scanning calorimetry (DSC) in the range from 80° C. to 170° C., preferably in the range from 135° C. to 165° C. and in particular in the range from 140° C. to 165° C.

The copolymers according to the invention of propylene with $C_2$–$C_{10}$-alk-1-enes generally have a melting point, determined by differential scanning calorimetry (DSC) (heating rate: 20° C./min.), in the range from 60° C. to 160° C., preferably in the range from 80 to 150° C. and in particular in the range from 100° C. to 150° C.

The pentad content mmmm, in other words the isotacticity, of the homopolymers according to the present invention, determined by $^{13}$C-NMR spectroscopy, is usually in the range from 60% to 99%, preferably in the range from 80% to 98%.

The proportion of xylene-soluble material in the propylene homopolymers and copolymers according to the present invention is usually less than 1.5% by weight, preferably less than 1.0% by weight.

The proportion of xylene-soluble material $X_S$ was determined as follows:

500 ml of distilled xylene (isomer mixture) were placed in a 1 liter three-neck flask fitted with stirrer, reflux condenser and thermometer and were heated to 100° C. At this temperature, the polymer was introduced, the mixture was subsequently heated to the boiling point of xylene and was refluxed for 60 minutes. Subsequently, the supply of heat was stopped, the mixture was cooled to 5° C. over a period of 20 minutes using a cooling bath and was then reheated to 20° C. This temperature was held for 30 minutes. The polymer which precipitated was filtered off and exactly 100 ml of the filtrate were placed in a previously tared 250 ml one-neck flask. The solvent was then removed on a rotary evaporator. The residue which was left was subsequently dried for 2 hours in a vacuum drying oven at 80° C./200 torr. After cooling, the flask was reweighed.

$$X_S = \frac{g \times 500 \times 100}{G \times V}$$

$X_S$=proportion of xylene-soluble material in %
g=amount found
G=weight of product sample
V=volume of filtrate used The chemically bound proportion of comonomer in the, preferably random, copolymers according to the present invention of propylene with $C_2$–$C_{10}$-alk-1-enes, measured by $^{13}$C-NMR spectroscopy, is generally in the range from 0.001 to 35 mol %, preferably in the range from 0.01 to 15 mol %, based on the copolymers. Suitable $C_2$–$C_{10}$-alkenes are, in particular, ethylene, 1-butene and mixtures thereof.

A well suited propylene polymer is the homopolypropylene NOVOLEN® M NX 50081 from Targor GmbH (previously BASF Aktiengesellschaft).

The moldings according to the present invention (injection-molded articles) are generally produced using the customary injection molding processes known to those skilled in the art.

The E modulus of the propylene homopolymers and copolymers according to the present invention, measured in a tensile test in accordance with ISO 527, is generally in the range from 1300 to 7500, preferably in the range from 1500 to 7500.

The haze, as a complementary value to transparency, determined in accordance with ASTM D 1003, is less than 10%, preferably less than 8%, for the propylene homopolymers and copolymers according to the present invention.

The injection-molded articles according to the present invention can further comprise the customary thermoplastic additives in the customary amounts. Possible additives are antistatic agents, lubricants such as fatty acid amides, for example erucamide, stabilizers, neutralizing agents such as calcium stearate, pigments and also inorganic fillers such as talc, aluminum oxide, aluminum sulfate, barium sulfate, calcium magnesium carbonate, silicon dioxide, titanium dioxide and glass fibers or else organic fillers such as polyesters, polystyrene, polyamide and halogenated organic polymers.

Other preferred additives are nucleating agents such as talc, alkali metal salts or aluminum salts of carboxylic and alkylaryl acids, certain polymers such as polyvinylcyclohexane or polycyclopentene and polyhydroxy compounds such as sorbitol derivatives. Particular preference is given to sorbitol derivatives.

The propylene homopolymers and copolymers according to the present invention are well suited to producing moldings, preferably hollow bodies, in particular injection-molded articles for a variety of applications, as described by way of example in the following.

The propylene homopolymers and copolymers according to the present invention are suitable for uses (applications)
in the audio/video/computer sector
  eg. CD/CD-ROM packaging, cassette bodies (audio/video), boxes for floppy disks and tapes;
in the medical sector
  eg. Petri dishes, cuvettes/blood analysis tubes, pipettes, disposable pipette tips, drug packaging, in particular vials or lids, syringe barrels, milk pumps, packaging for tablets, mouthpieces for inhalers;
in dairy and food packaging
  eg. yoghurt tubs, dessert tubs, cheese packaging, pate packaging, gourmet food tubs, containers for single portions, trays for prepackaged meals, spice containers;
in the household article sector
  eg. drinking cups, containers for food, Ferrero®, Tupperware®, microwave applications, catering, blow-molded containers, water softening filters, brewery filters, clothes hangers, insulated drink containers, baby bottles, lids for baby bottles, parts for dummies;
in the office supplies sector
  eg. trays, filing boxes, magazine racks, box files, drawing requisites;
in the cosmetics packaging sector
  eg. ointment containers, caps, cartridges, boxes for wet wipes, pots, roll-on deodorant containers (ball and housing);
for closures, caps, lids of all sorts; laundry detergent packaging eg. dosing balls;

in the sanitary sector eg. toothbrush cases, toothpaste containers such as tubes and dispensers, beakers, brush bodies, bathroom shelves, bathroom furniture, mirror cabinets, toilet seats, hotel soap dispensers;

in the electrical appliance sector eg. coffee machine housings, sightglasses for coffee machines or water boilers, lids for egg cookers, refrigeration appliance internal components such as vegetable compartments, optical waveguides eg. in automobiles and passenger cars, clothes irons, water containers such as lids for water boilers, lamp covers;

in the storage container and transport container sector eg. containers for screws, containers for tools, sightglasses, containers for transporting animals, jewelry and gift packaging such as Swatch® packaging, baskets, wall holders;

in the writing implements sector eg. bodies of pens;

in the toy sector eg. packaging for playing cards, containers for storing toys eg. for Lego® building blocks;

in the laboratory requisites sector eg. measuring cups, measuring cylinders, laboratory flasks eg. for aggressive substances, buckets.

Furthermore, the propylene homopolymers and copolymers according to the present invention are well suited for producing moldings, preferably injection-molded articles eg. cartridges, clips and rings, eg. for curtains, boards for computer chips, protective casings for computer chip boards, cases;

in the tool sector eg. tool handles;

in the motor vehicle sector eg. covers for interior lights, substitutes for glass, polycarbonate or polystyrene;

in the furniture sector, preferably outdoor furniture, eg. transparent, colored or non-colored garden furniture.

We claim:

1. Injection-molded CD packaging or injection-molded CD-ROM packaging comprising an essentially isotactic homopolymer of propylene or a copolymer of propylene with $C_2$–$C_{10}$-alk-1-enes, which polymer is obtained by polymerization of the corresponding monomers using metallocene catalysts, wherein the homopolymer of propylene has (1) a Melt Flow Rate of 40–80 g/10 min. (measured at 230° C. with a load of 2.16 kg in accordance with DIN 53735);

(2) a molecular weight distribution of 1.2 to 2.5 (Mw/Mn);

(3) a melting point of 140–165° C. (DSC);

(4) a pentad content mmmm of 80% to 98% (determined by 13C-NMR);

(5) a xylene-soluble content of less than 1% by weight;

(6) an E modulus of 1500 to 7000 (measured in a tensile test by ISO 527); and (7) a haze of less than 8% (determined by ASTMD 1003), and wherein the copolymer of propylene has (1) a Melt Flow Rate of 40–80 g/10 min.;

(2) a melting point of 100° to 150° C. (DSC);

(3) a Mw/Mn ratio of 1.2 to 2.5;

(4) a xylene-soluble content of less than 1% by weight;

(5) a chemically bound proportion of comonomer in the range of 0.01 to 15 mol %;

(6) an E modulus, measured in a tensile test, in the range of from 1500 to 7500 (tensile test in accordance with ISO 527); and (7) haze of less than 8% (determined in accordance with ASTM D 1003).

2. The injection-molded packaging of claim 1, wherein the copolymer of propylene is used for said packaging.

3. The injection-molded packaging of claim 1, wherein the homopolymer of propylene is used for said packaging.

4. A process for preparing CD packaging or CD-ROM packaging wherein propylene or a monomer mixture of propylene and at least one further $C_2$–$C_{10}$-alk-1-ene is polymerized by metallocene catalysts and the resulting essentially isotactic homopolymer of propylene or copolymer of propylene with $C_2$–$C_{10}$-alk-1-enes is injection molded to said CD packaging or CD-ROM packaging, wherein the homopolymer of propylene has (1) a Melt Flow Rate of 40–80 g/10 min. (measured at 230° C. with a load of 2.16 kg in accordance with DIN 53735);

(2) a molecular weight distribution of 1.2 to 2.5 (Mw/Mn);

(3) a melting point of 140–165° C. (DSC);

(4) a pentad content mmmm of 80% to 98% (determined by 13C-NMR);

(5) a xylene-soluble content of less than 1% by weight;

(6) an E modulus of 1500 to 7000 (measured in a tensile test by ISO 527); and (7) a haze of less than 8% (determined by ASTMD 1003), and wherein the copolymer of propylene has (1) a Melt Flow Rate of 40–80 g/10 min.;

(2) a melting point of 100° to 150° C. (DSC);

(3) a Mw/Mn ratio of 1.2 to 2.5;

(4) a xylene-soluble content of less than 1% by weight;

(5) a chemically bound proportion of comonomer in the range of 0.01 to 15 mol %;

(6) an E modulus, measured in a tensile test, in the range of from 1500 to 7500 (tensile test in accordance with ISO 527); and (7) haze of less than 8% (determined in accordance with ASTM D 1003).

5. The process of claim 4, wherein the homopolymer of propylene is used for said packaging.

6. The process of claim 4, wherein a copolymer of propylene is used for said packaging.

* * * * *

UNITED STATES PATENT AND TRADEMARK OFFICE
CERTIFICATE OF CORRECTION

PATENT NO.    : 6,537,478 B1
DATED         : March 25, 2003
INVENTOR(S)   : Grasmeder et al.

It is certified that error appears in the above-identified patent and that said Letters Patent is hereby corrected as shown below:

Title page,
Item [57], ABSTRACT,
Line 2, "$C_2 14 C_{10}$-alk-1-enes" should be -- $C_2$-$C_{10}$-alk-1-enes --.

Signed and Sealed this

Fifth Day of August, 2003

JAMES E. ROGAN
*Director of the United States Patent and Trademark Office*